United States Patent [19]

Tersteeg et al.

[11] 4,347,750

[45] Sep. 7, 1982

[54] POTENTIOMETRIC METERING APPARATUS

[75] Inventors: Glenn E. Tersteeg, Honeoye Falls; Anthony P. DiFulvio, Rochester, both of N.Y.

[73] Assignee: Eastman Kodak Company, Rochester, N.Y.

[21] Appl. No.: 159,561

[22] Filed: Jun. 16, 1980

[51] Int. Cl.³ ..................... G01N 1/14; G01N 27/46; G01N 35/06

[52] U.S. Cl. ................................ 73/864.31; 141/130; 422/64; 422/100

[58] Field of Search ........... 73/864.11, 864.12, 864.21, 73/864.31, 864.22; 422/64, 100; 141/130, 90

[56] References Cited

U.S. PATENT DOCUMENTS

| | | | |
|---|---|---|---|
| 3,192,969 | 7/1965 | Baruch et al. | 73/864.12 |
| 3,197,285 | 7/1965 | Rosen | 422/100 |
| 3,681,030 | 8/1972 | Natelson | 73/864.11 |
| 3,767,364 | 10/1973 | Ritchie et al. | 141/130 X |
| 3,917,455 | 11/1975 | Bak et al. | 422/65 X |
| 3,988,921 | 11/1976 | Lightner | 73/864.11 X |
| 4,076,503 | 2/1978 | Atwood et al. | 141/90 X |
| 4,172,777 | 10/1979 | Yamamoto et al. | 204/195 R |
| 4,228,831 | 10/1980 | Kerns | 73/864.12 |
| 4,268,477 | 5/1981 | Herzstark | 422/64 |

Primary Examiner—Daniel M. Yasich
Attorney, Agent, or Firm—D. I. Hague

[57] ABSTRACT

An analyzer for biological fluids includes a sample fluid metering device that is movable to a first metering position located directly over a generally planar test element supported in a metering station, and a reference fluid metering apparatus that is movable to a second metering position closely adjacent the first metering position. The reference fluid metering apparatus comprises a reference fluid supply reservoir supported in a location spaced from the metering station, an aspirator operable to aspirate reference fluid from the reservoir and to deposit the fluid on the test element positioned at the metering station and a cam and gear arrangement driven by a single drive motor for moving the aspirator linearly toward and away from the supply reservoir and toward and away from the metering station and for pivotally moving the aspirator between a position spaced from the supply reservoir and a position spaced from the metering station.

5 Claims, 4 Drawing Figures

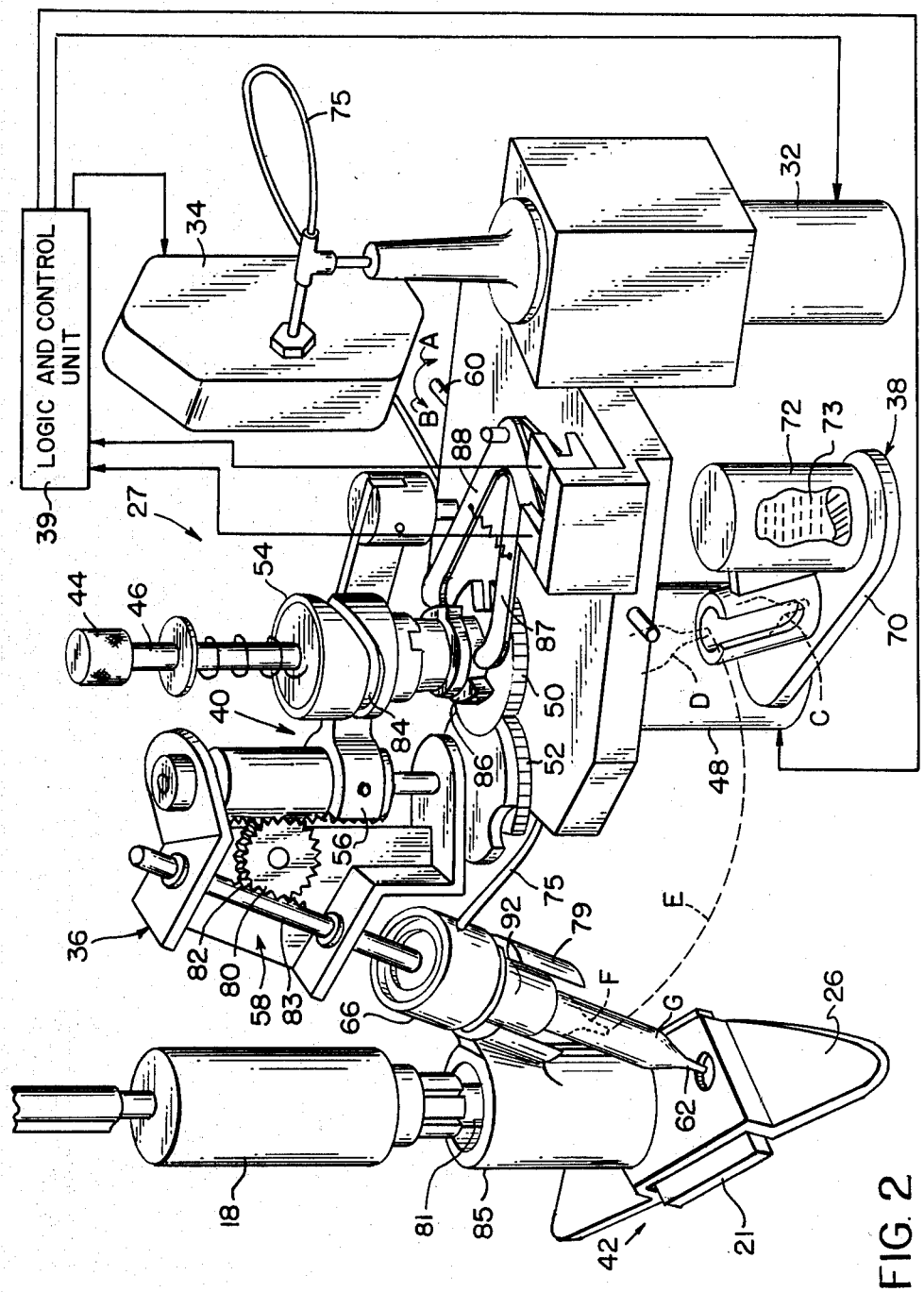

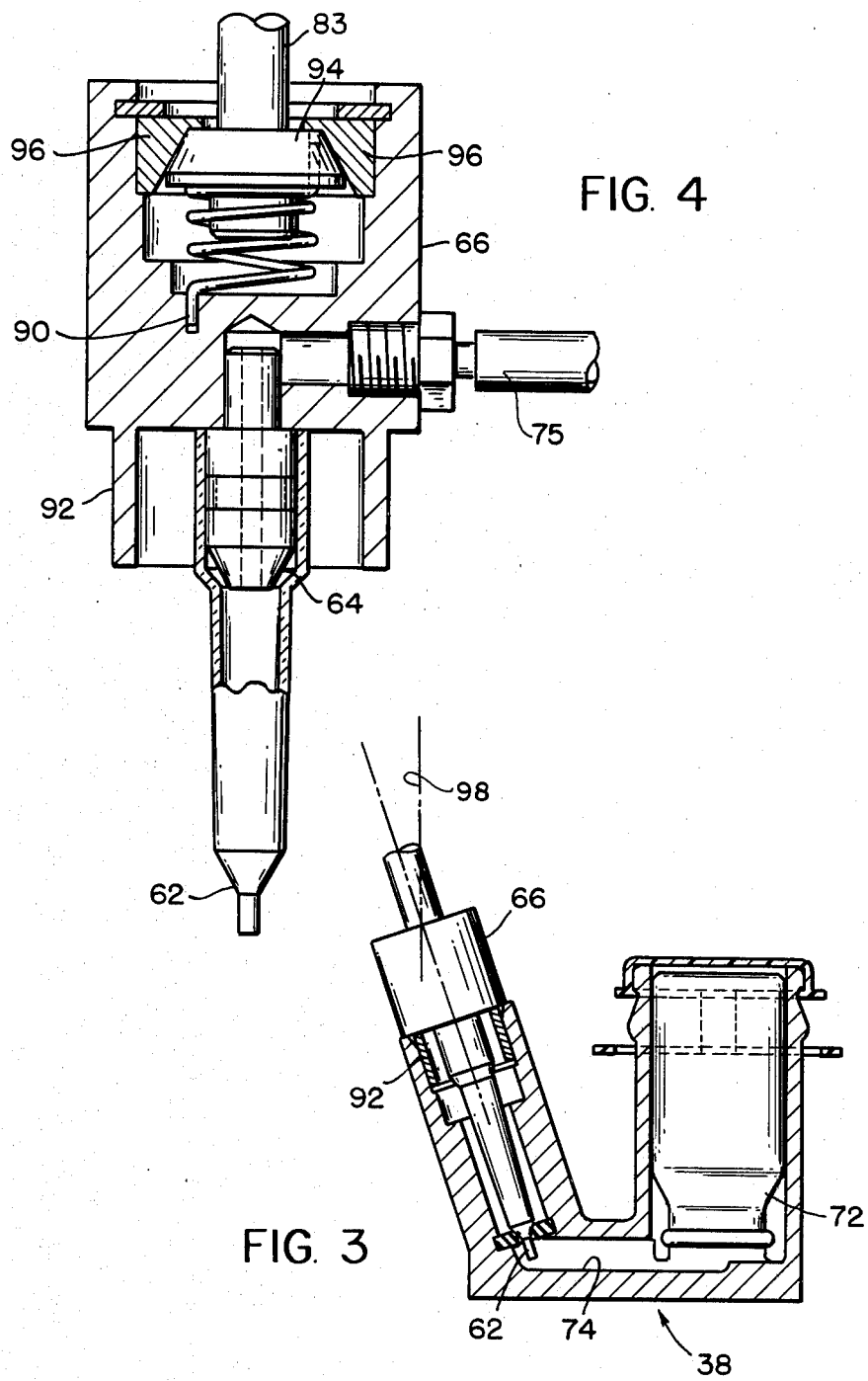

POTENTIOMETRIC METERING APPARATUS

CROSS-REFERENCE TO RELATED APPLICATIONS

Reference is made to commonly assigned U.S. Pat application Ser. No. 159,564, now U.S. Pat. No. 4,296,070, entitled SLIDE DISTRIBUTOR FOR A CHEMICAL ANALYZER, filed on even date herewith in the names of Montalto et al.

BACKGROUND OF THE INVENTION

1. Field of the Invention

This invention relates to apparatus for use in the chemical analysis of biological fluids and, more particularly, to apparatus for automated metering of biological fluids onto test elements.

2. Description Relative to the Prior Art

A number of automated systems have been developed for performing quantitative chemical analysis of biological fluids, such as blood serum. Most of the commercially available systems utilize liquid reagents and require analyzer equipment having complex solution handling and transport capabilities. Recent developments, however, have provided test elements for biological fluid analyzers in essentially planar, dry form. One form of such a test element is disclosed in U.S. Pat. No. 4,053,381 to Hamblin, et al granted on Oct. 11, 1977. This patent describes a test element of the type which comprises a pair of electrodes, selective to the ion activity of choice, supported on a substrate and having a generally planar strip form, and a bridge used to promote ionic migration between a reference fluid and a patient sample fluid. The electrical signal derived from the pair of electrodes is indicative of the test ion activity and thus of the ion concentration. Another form of test element is disclosed in commonly-owned U.S. Pat. No. 3,992,158 to Przybylowicz, et al granted on Nov. 16, 1976. The test element disclosed in this patent is formed as a multi-layered element containing the necessary reagents for reaction with components of a biological fluid deposited thereon. Certain reactions colorimetrically produce a change in optical density in the element which is sensed by a reflectometer, the amount of light reflected from the element varying in accordance with the reaction and being indicative of the amount of a particular analyte present in the fluid.

In performing the chemical analysis of biological fluids such as blood serum, it is frequently desirable to process samples of such fluids on test elements of both the potentiometric and colorimetric types. The former requires the metering of small precise amount of reference fluid and patient sample fluid onto the test element whereas the latter requires only the metering of the patient sample fluid. An analyzer adapted to process both potentiometric and colorimetric test elements is disclosed in the aforementioned commonly-assigned U.S. pat. application Ser. No. 159,564, now U.S. pat. No. 4,296,070. In order to manufacture such a dual capability analyzer at a commercially acceptable cost and size, the individual analyzer components must be compact, efficient, and able to function in close proximity with other components. More specifically, a reference fluid metering device must be provided for use in conjunction with the patient sample fluid metering device for depositing a predetermined quantity of reference fluid onto a potentiometric test element supported in a metering station of the analyzer. The potentiometric test elements used in the analyzer have exterior dimensions of approximately 2.5 mm by 3.0 mm and require the reference fluid metering device to deposit the reference fluid onto the test element at a position spaced only approximately 1 mm from the patient sample fluid concurrently deposited on the test element by the sample fluid metering device.

SUMMARY OF THE INVENTION

In accordance with the present invention reference fluid metering apparatus is provided for use with a sample fluid metering device to substantially concurrently deposit a sample fluid onto a first test area and a reference fluid onto a second test area of a generally planar potentiometric test element supported in a metering station. The reference fluid metering apparatus comprises reference fluid supply means supported in a location spaced from the metering station, dispensing means including a metering tip for receiving a reference fluid located in the supply means and for delivering a predetermined quantity of the reference fluid to the second test area of the test element, the dispensing means being movable between a first position overlying the supply means and a second position in which the metering tip is positioned over the second test area and closely adjacent the first test area of the test element and disposed at an angle to the sample fluid metering device, drive means for moving the dispensing means between the first and second positions and logic and control means for automatically controlling the operations of the sample fluid metering device, dispensing means and drive means to effect the delivery of fluids to the first and second test areas at substantially the same time.

In a preferred embodiment of the invention, a metering tip is releasably mounted on an articulated aspirator of the dispensing means so that the metering tip is disposed at an angle of approximately 18° with respect to the vertical axis of the metering apparatus. Disposing the metering tip at an angle assists in the positioning of the metering apparatus at the metering station in close proximity to the sample fluid metering device and the articulated aspirator allows positive yet compliant seating of the metering tip in the metering station and also into the reference fluid supply means. The invention and its object and advantages will become more apparent by referring to the accompanying drawing and to the ensuing detailed description of the preferred embodiment.

BRIEF DESCRIPTION OF THE DRAWINGS

FIG. 2 is a perspective view of a preferred embodiment of the reference fluid metering apparatus showing such apparatus in a position overlying the metering station;

FIG. 3 is an elevational view, partially in section, showing a portion of the metering apparatus in a position overlying the supply reservoir and with the metering tip inserted into the reservoir; and FIG. 4 is an elevational view, partially in section, showing the mounting arrangement for articulating the aspirator of the metering apparatus.

DETAILED DESCRIPTION OF THE PREFERRED EMBODIMENT

Figure 1:
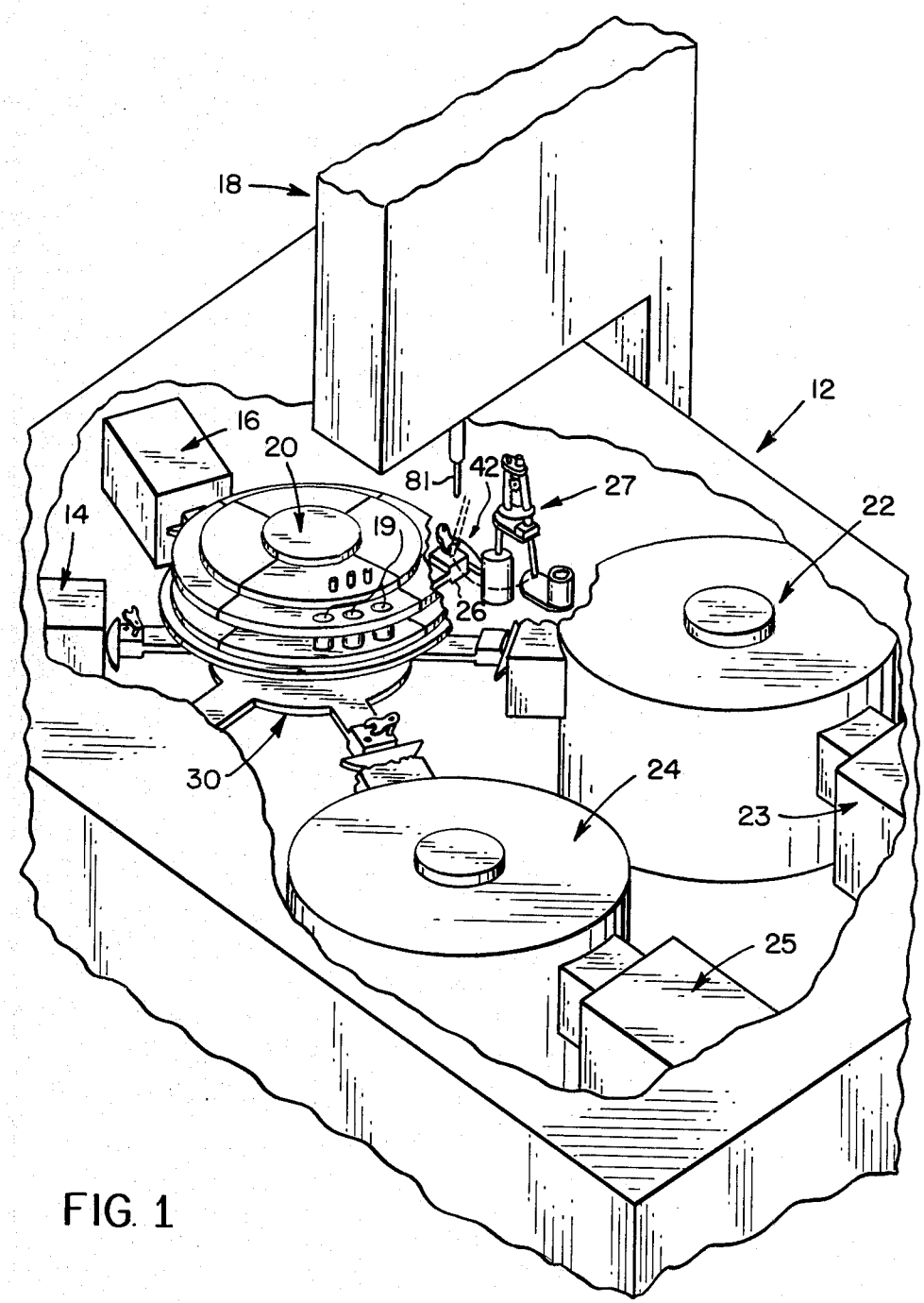
FIG. 1 is a perspective view, of a chemical analyzer, with parts broken away to show the analyzer elements including the reference fluid metering apparatus of the invention.

Because chemical analyzers for biological fluids such as blood serum are well known, the present description will be directed in particular to elements forming part of, or cooperating more directly with, apparatus constructed in accordance with the present invention. It is to be understood that analyzer elements not specifically shown or described may take various forms well known to those having skill in the art.

With reference now to the drawings, there is shown analyzer apparatus 12 of the type which processes test elements of the potentiometric type fed from a supply 16 and test elements of a colorimetric type fed from a supply 14. A sample fluid metering device 18 is adapted to aspirate patient sample fluid from one of a plurality of cups 19 in a sample tray 20, to move to a metering position located directly over a test element 21 supported in a metering station 42 by a slide holder 26 of a test element distributor 30 and to deposit a precise quantity of the sample fluid onto a first area of the test element. A reference fluid metering apparatus 27, constructed in accordance with the teachings of the present invention and described in detail herein below, works in conjunction with the sample fluid metering device 18 to deposit a reference fluid onto a second area of the test elements of the potentiometric type. After the metering operations, test elements of the potentiometric type are deposited in an incubator 22 from the distributor 30 and test elements of the colorimetric type are deposited in an incubator 24. Incubators 22 and 24 are adapted to cooperate respectively with read stations 23 and 25 which, after a suitable incubation period, measure a change in the test elements as a result of the fluid deposited thereon.

The reference fluid metering apparatus 27 must be capable of repeatedly and accurately dispensing very small quantities of reference fluid onto potentiometric test elements 21 substantially concurrently with the dispensing of patient sample fluid onto the elements 21 by the sample fluid metering device 18. For example, a preferred embodiment of the reference fluid metering apparatus 27 dispenses 10 microliters ±0.5 microliters of reference fluid onto a potentiometric test element 21 having exterior dimensions of approximately 2.5 millimeters (mm) by 3.0 mm within a one second time window of the dispense of patient sample fluid by the sample fluid metering device 18. The reference and sample fluids are dispensed by the apparatus 27 and device 18, respectively onto the test element 21 at positions which are spaced approximately 1 mm apart. As shown in FIG. 2 the reference fluid metering apparatus 27 comprises a pump 32, a pressure transducer 34, a metering arm assembly 36, a reference fluid supply resevoir 38 and a drive mechanism generally denoted 40 for moving the assembly 36 between a first position overlying the supply resevoir 38 and a second position overlying the metering station 42.

To prepare the metering apparatus 27 for operation a manual control knob 44 on a drive shaft 46 of a bi-direction motor 48 is turned by the analyzer operator. Rotation of the knob 44 manually operates the drive mechanism 40, which comprises the motor 48 and shaft 46, a rack-pinion-rack gear drive 58, mutilated assembly swing gears 50 and 52 respectively mounted on the shaft 46 and the drive 58, a cam 54 also mounted on the shaft 46 and a cam follower 56 connected to the cam 54 and the drive 58, to move the metering apparatus 27 to a select position where it can be unlatched by a latch mechanism (not shown) and then pivoted about a support shaft 60 in the direction of arrow A for accessability. A metering tip 62 is manually pushed onto a tapered tubular member 64 of an articulated aspirator 66. (see FIG. 4.) The metering tip 62 is mounted on the aspirator 66 so that the tip is disposed at an angle of approximately 18° with respect to the vertical axis 98 of the metering apparatus 27. The operator also turns a reservoir block 70 over, inserts a bottle 72 of reference fluid 73 in the upright position into the block and then turns the integrated reservoir 38 (block and bottle) over so that the bottle mouth is down. The balance of forces on the column of fluid 73 in the bottle 72 causes the fluid 73 to run out of the bottle only until a channel 74 in the block 70 is full. As fluid 73 is aspirated into the metering tip 62, surface tension at the bottle mouth and a negative pressure over the fluid in the bottle 72 support the fluid head in a controlled manner so that the fluid in the bottle replaces and maintains the original level in the channel 74. After insertion of a metering tip 62 and a reference fluid supply bottle 72, the metering apparatus 27 is pivoted about shaft 60 in the direction of arrow B, relatched by the latch mechanism and returned by manual operation of the drive mechanism 40, via knob 44, to the first (home) position, shown in solid lines in FIG. 3 and in dotted lines in FIG. 2, in which the assembly 36 overlies the supply reservoir 38. In this position the metering tip 62 is inserted into the channel 74 where it acts as a cap for the reservoir 38.

In operation, a keyboard of a logic and control unit (39) is used by the operator to provide test input data to the analyzer 12. The logic and control unit can be selected from a variety of commercially available mini computers or microprocessors. The programming of such a computer or processor can be by means of hardware or by an appropriate program as is well known. At the beginning of the reference fluid dispensing cycle, the pump 32 and pressure transducer 34 are activated by the logic and control unit to produce a partial vacuum. "Dispensing cycle" is used herein to refer to the sequence of movements which occur in the elements of the metering apparatus 27 for the dispensing of reference fluid 73 onto a single test element 21. The partial vacuum is applied through a connector 75 to the aspirator 66 for a period of time sufficient to aspirate enough fluid 73 into the metering tip 62 to cover a patient's reference fluid test requirements. After aspiration, 10 microliters of reference fluid 73 are dispensed back into the reservoir 38. If the reservoir is empty, the pressure transducer 34 will sense the absence of a rise in pressure and provide a reservoir empty signal indicating to the operator that the reference fluid supply bottle 72 should be replaced.

To move the assembly 36 from the first (home) position (labeled "C" in FIG. 2) overlying the supply reservoir 38 to a second position (labeled "G" in FIG. 2) overlying the metering station 42, the drive motor 48 is energized to rotate the drive shaft 46, and the mutilated gear 50 and cam 54 which are mounted thereon, in a first direction. In the home position of the assembly 36, the gears 50 and 52 are not engaged so that the initial rotation of the gear 50 in the first direction provides no pivotable movement to the assembly. However, the initial rotation of the cam 54 in the first direction causes the cam follower 56 to lower a first rack gear 78 of the rack-pinion-rack drive 58. Lowering the first rack gear 78 rotates a pinion 80 in a clockwise direction and raises a second rack gear 82 formed on a shaft 83 on which the aspirator 66 and metering tip 62 are mounted. After raising the assembly 36 to a third position (labeled "D" in FIG. 2) approximately 0.6 inches above the reservoir 38, the cam 54 and cam follower 56 enter a dwell region 84 as the mutilated gears 50 and 52 mesh and drive the assembly 36 through a 120° clockwise rotation (shown in a dash line labeled "E" in FIG. 2) in the horizontal plane. When the gears 50 and 52 no longer mesh, the assembly 36 is located at a fourth position (labeled "F" in FIG. 2) above the metering station 42, and the cam 54 and cam follower 56 leave their dwell region and again operate so as to raise the rack gear 78. Raising the rack gear 78 rotates the pinion 80 in a counterclockwise direction and lowers the rack gear 82 approximately 0.6 inches so that the assembly 36 is located at the second position (labeled "G" in FIG. 2) overlying the metering station 26 with the metering tip 62 positioned in a metering guide member 79 located directly over a potentiometric test element 21 and closely adjacent a metering guide member 85 for the sample fluid metering device 18. The angular disposition of the metering tip 62 permits the tip 62 to be positioned in the metering station 42 in close proximity to the metering tip 81 of the sample fluid metering device 18.

A cam position sensor 86 mounted on the shaft 46 cooperates with a first cam follower 87 to provide a signal to the analyzer logic and control unit when the assembly 36 reaches its second position. In response to the receipt of this signal, the logic and control unit de-energizes the drive motor 48, activates the pump 32 to dispense, under the control of the transducer 34, approximately 10 microliters of reference fluid from the aspirator 66 onto the test element 21 and then re-energizes the motor 48 for rotation in a second, opposite direction. Rotation of the motor 48 in the second direction causes the assembly 36 to reverse its previously described movements. Thus the cam 54 and cam follower 56 first cooperate to raise the assembly 36 approximately 0.6 inches to the fourth position ("F"), then the gears 50 and 52 mesh to drive the assembly through 120° of counterclockwise rotation in the horizontal plane to the third position ("D") and finally the cam 54 and cam follower 56 again cooperate to lower the assembly to the first position ("C") in which the metering tip 62 caps the reservoir 38. When the assembly 36 reaches the first position overlying the supply reservoir 38, the cam position sensor 86 and a second cam follower 88 cooperate to provide a signal to the logic and control unit which then deactivates the motor 48. The reference fluid metering apparatus 27 remains inactive at the first position until the distributor 30 delivers the next potentiometric test element to the metering station 26. The dispensing cycles then repeat until all the potentiometric test elements for a given patient are spotted with reference fluid. Upon returning to the reservoir 38 the last time all unused fluid in the metering tip 62 is discharged back into the reservoir so that the next patient's aspirator requirements can be accurately controlled.

As shown in FIG. 4, the aspirator 66 is articulated to provide positive yet compliant seating of the metering tip 62 within the aspirator when the tip is positioned in the metering guide member 79 or in the channel 74 of the reservoir 38. A spring 90 is mounted within a metering tip shroud 92 between the tubular member 64 and a beveled flange 94 and resiliently urges the flange into seating engagement with a similarly beveled seat 96. In the preferred embodiment of the invention, the aforedescribed seating arrangement provides a compliance for the metering tip 62 of ±0.04 inches in the lateral direction, +0.07 inches in the vertical direction and approximately 30° in angular swing away from the vertical axis 98 of the metering apparatus 27.

The invention has been described in detail with particular reference to a preferred embodiment thereof, but it will be understood that variations and modifications can be effected within the spirit and scope of the invention.

We claim:

1. Reference fluid metering apparatus for use with a sample fluid metering device to substantially concurrently deposit a sample fluid onto a first test area and a reference fluid onto a second test area of a generally planar, potentiometric test element supported in a metering station, the reference fluid metering apparatus comprising:

(a) reference fluid supply means supported in a location spaced from the metering station;
    (b) dispensing means including a metering tip angularly arranged for receiving reference fluid located in the supply means and for delivering a predetermined quantity of the reference fluid to the second area of the test element, the dispensing means being selectively movable between a at least a position overlying the supply means and a second position in which the metering tip is positioned over the second test area and closely adjacent the first test area of the test element and disposed at an angle to the sample fluid metering device;
    (c) drive means for moving the dispensing means between the first and second positions; and
    (d) logic and control means for automatically controlling the operations of the sample fluid metering device, dispensing means and drive means to effect the delivery of fluids to the first and second test areas at substantially the same time.

2. The reference fluid metering apparatus according to claim 1 wherein the metering tip is releasably mounted on the dispensing means at an angle of approximately 18° with respect to the sample fluid metering device.

3. The reference fluid metering apparatus according to claim 1 wherein the reference fluid supply means comprises a fluid supply reservoir having an opening therein from which fluid is delivered into the dispensing means and the metering tip is received in the opening where it serves as a cap for the reservoir when the dispensing means is moved to the first position.

4. The reference fluid metering apparatus according to claim 1 wherein the dispensing means includes an articulated member which allows positive yet compliant seating of the metering tip within the articulated member.

5. The reference fluid metering apparatus according to claim 1 wherein the drive means includes a motor which is energizable in a first direction of rotation and a second direction of rotation, a cam and a cam follower coupled between the motor and the dispensing means for effecting linear movement of the dispensing means, first and second mutilated gears coupled between the motor and the dispensing means for effecting pivotal movement of the dispensing means and switch means responseive to the position of the dispensing means for selectively energizing the motor in the first and second directions of rotation.

* * * * *